(12) United States Patent
Proll et al.

(10) Patent No.: US 7,348,443 B2
(45) Date of Patent: Mar. 25, 2008

(54) METHOD FOR PRODUCING PARTIAL OXIDATION PRODUCTS AND/OR PARTIAL AMMOXIDATION PRODUCTS OF AT LEAST ONE OLEFINIC HYDROCARBON

(75) Inventors: Theo Proll, Bad Duerkheim (DE); Otto Machhammer, Mannheim (DE); Goetz-Peter Schindler, Mannheim (DE); Klaus Joachim Mueller-Engel, Stutensee Blankenloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 652 days.

(21) Appl. No.: 10/482,191

(22) PCT Filed: Jun. 21, 2002

(86) PCT No.: PCT/EP02/06878

§ 371 (c)(1),
(2), (4) Date: Dec. 29, 2003

(87) PCT Pub. No.: WO03/011804

PCT Pub. Date: Feb. 13, 2003

(65) Prior Publication Data

US 2004/0181083 A1    Sep. 16, 2004

(51) Int. Cl.
*C07D 301/06* (2006.01)
(52) U.S. Cl. .................................... 549/523
(58) Field of Classification Search ............... 549/523
See application file for complete search history.

(56) References Cited

U.S. PATENT DOCUMENTS

| 3,882,159 A | 5/1975 | Callahan et al. |
| 5,312,931 A | 5/1994 | Stavinoha et al. |

FOREIGN PATENT DOCUMENTS

| DE | 1 254 137 | 11/1967 |
| DE | 2 159 346 | 6/1972 |
| DE | 2 106 796 | 8/1972 |
| DE | 2 351 151 | 4/1974 |
| DE | 33 13 573 | 10/1983 |
| DE | 35 21 458 | 12/1985 |
| DE | 101 01 695 | 7/2002 |
| EP | 0 117 146 | 8/1984 |
| EP | 117 146 | 8/1984 |
| EP | 0 328 280 | 8/1989 |
| EP | 328 280 | 8/1989 |
| EP | 0 372 972 | 6/1990 |
| EP | 0 731 080 | 9/1996 |
| EP | 731 080 | 9/1996 |
| WO | 01/96270 | 12/2001 |
| WO | 01 96270 | 12/2001 |

*Primary Examiner*—Taofiq Solola
(74) *Attorney, Agent, or Firm*—Oblon, Spivak, McClelland, Maier & Neustadt, P.C.

(57) ABSTRACT

Partial oxidation products and/or ammoxidation products of an olefinic hydrocarbon A' are prepared by a process in which said olefinic hydrocarbon is produced during normal operation by partial dehydrogenation and/or oxydehydrogenation of hydrocarbon A and fed in from another source during partial or complete nonoperation of the dehydrogenation and/or oxydehydrogenation.

12 Claims, 1 Drawing Sheet

US 7,348,443 B2

Figure 1:
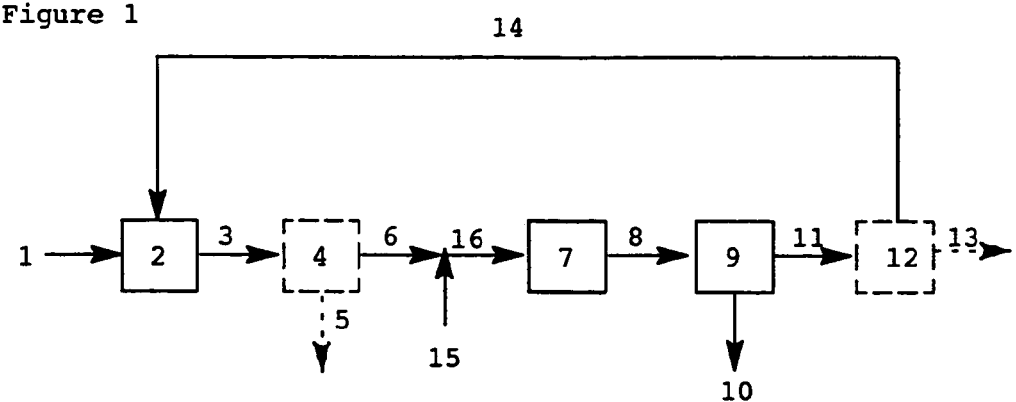

METHOD FOR PRODUCING PARTIAL OXIDATION PRODUCTS AND/OR PARTIAL AMMOXIDATION PRODUCTS OF AT LEAST ONE OLEFINIC HYDROCARBON

BACKGROUND OF THE INVENTION

1. Field of the Invention

The present invention relates to a process for the preparation of partial oxidation products and/or partial ammoxidation products of at least one olefinic hydrocarbon A', in which A) in a first reaction zone A, at least one paraffinic hydrocarbon A is subjected to a partial dehydrogenation and/or oxydehydrogenation with formation of a product mixture A which contains an unconverted amount of at least one hydrocarbon A and at least one olefinic hydrocarbon A' formed by the partial dehydrogenation and/or oxydehydrogenation, B) a portion or the total amount of the components contained in the product mixture A and differing from the at least one paraffinic hydrocarbon A and the at least one olefinic hydrocarbon A' is separated from said product mixture A, if required in a separation zone, to give a product mixture A', and either the product mixture A or the product mixture A' is used for feeding an oxidation and/or ammoxidation zone B and, in the oxidation and/or ammoxidation zone B, at least the at least one olefinic hydrocarbon A' is subjected to a partial oxidation and/or ammoxidation with formation of a product mixture B which contains, as desired product, at least one partial oxidation and/or ammoxidation product B of the at least one olefinic hydrocarbon A', C) the desired product is separated from the product mixture B in a working-up zone C and at least a portion of the unconverted at least one paraffinic hydrocarbon A contained in the product mixture B is recycled as paraffinic recycle hydrocarbon A into the reaction zone A and D) from time to time, in a nonoperating phase, at least a part of the reaction zone A is not operated for the purpose of the partial dehydrogenation and/or oxydehydrogenation of the at least one paraffinic hydrocarbon A.

Partial oxidation products of olefinic hydrocarbons are important intermediates, for example for the preparation of polymers.

In this document, oxydehydrogenation is understood as meaning a dehydrogenation which is forced by the oxygen present and in which no hydrogen is formed in the intermediate stage.

In this document, a paraffinic hydrocarbon is to be understood as meaning a saturated hydrocarbon. In this document, an olefinic hydrocarbon is to be understood as meaning a hydrocarbon which has at least one ethylenically unsaturated double bond (examples are propylene, isobutene and butadiene).

In this document, the paraffinic and the olefinic hydrocarbons contain, as a rule, not more than ten carbon atoms. In this document, the paraffinic and the olefinic hydrocarbons preferably have two, three or four carbon atoms. Preferred paraffinic hydrocarbons in this document are ethane, propane and butanes. In this document, preferred olefinic hydrocarbons are propylene (propene), ethylene (ethene) and butenes. In this document, the preferred partial oxidation and/or ammoxidation products of olefinic hydrocarbons are acrolein, acrylic acid, ethylene oxide, methacrolein, methacrylic acid, propylene oxide, acrylonitrile and methacrylonitrile.

In this document, a complete oxidation of an olefinic hydrocarbon is understood as meaning that all the carbon contained in the olefinic hydrocarbon is converted into oxides of carbon (CO, $CO_2$). In this document, all reactions of an olefinic hydrocarbon with molecular oxygen which differ therefrom are subsumed under the term partial oxidation. The additional involvement of ammonia in the reaction is referred to as ammoxidation.

DESCRIPTION OF THE BACKGROUND

It is generally known that numerous key chemicals can be produced by partial oxidation and/or ammoxidation of olefinic hydrocarbons. Examples are the conversion of propylene to acrolein and/or acrylic acid (cf. for example DE-A 2 351 151), the conversion of ethylene to ethylene oxide (cf. for example German Published Application DAS 1,254,137, DE-A 2 159 346, EP-A 372 972 and WO-89/0710), the conversion of butadiene into maleic anhydride (cf. for example DE-A 2 106 796 and DE-A 1 624 921), the conversion of butadiene into vinyloxirane (cf. for example U.S. Pat. No. 5,312,931), the conversion of propylene into acrylonitrile (cf. for example DE-A 2 351 151), the conversion of isobutene into methacrolein (cf. for example DE-A 10101695), the conversion of isobutene into methacrylonitrile (cf. for example U.S. Pat. No. 3,882,159) and the conversion of propylene into propylene oxide (cf. for example EP-A 372 972).

As a rule, the preparation processes are heterogeneously catalyzed gas-phase oxidations and/or gas-phase ammoxidations. The ammoxidation usually differs from the oxidation because of the presence of ammonia. With a skillful choice of the ammonia content, the gas-phase oxidation and the ammoxidation of an olefinic hydrocarbon can also be carried out simultaneously in a gas mixture. The oxidizing agent usually used is molecular oxygen, which can be added, for example in pure form or as a mixture with gases substantially inert with respect to the partial oxidation (e.g. air), to the reaction gas starting mixture. As a rule, multimetal oxides are used as catalysts and frequently the reactants molecular oxygen and olefinic hydrocarbon in the reaction gas starting mixture are diluted with an inert gas (e.g. $N_2$, $H_2O$, CO, $CO_2$, He and/or Ar, etc.).

However, processes for the liquid-phase partial oxidation and/or liquid-phase partial ammoxidation of olefinic hydrocarbons are also known.

Usually a crude olefinic hydrocarbon which normally contains at least 90%, based on its weight, of olefinic hydrocarbon in addition to secondary components is used as olefinic starting hydrocarbon for the partial oxidations and/or partial ammoxidations evaluated in the prior art. Frequently, the content of olefinic hydrocarbon is even at least 95% or at least 99%, based on its weight.

The isolation of such comparatively pure crude olefinic hydrocarbons is relatively complicated and expensive. It generally starts from paraffinic hydrocarbons and usually comprises at least one purification stage in which unconverted paraffinic hydrocarbon is separated from olefinic hydrocarbon formed, by means of physical methods (cf. for example DE-A 3521458). This separation generally involves high capital costs and, owing to the similarity of olefinic and paraffinic hydrocarbons, is very energy-consumptive. It is therefore usually used only in combination with refinery crackers and steam crackers and is viable only because the predominant amount of the crude olefinic hydrocarbons thus obtained is required in large amounts for subsequent polymerizations on the one hand and on the other hand is associated with a high net product.

The amount of these crude olefinic hydrocarbons used in partial oxidations and/or partial ammoxidations tends to be of minor importance and is virtually a minor secondary stream used as required. As a consequence of this, crude olefinic hydrocarbon produced in this manner has an acceptable raw material price even for partial oxidations and/or partial ammoxidations.

This raw material price could however be significantly reduced if the described separation of paraffinic hydrocarbons and olefinic hydrocarbon formed is dispensed with and the resulting crude olefinic hydrocarbon is used as such for the subsequent partial oxidation and/or partial ammoxidation of the olefinic hydrocarbon. This is possible in principle because paraffinic hydrocarbons are generally substantially inert with respect to partial oxidations and/or partial ammoxidations of olefinic hydrocarbons, particularly those which are heterogeneously catalyzed in the gas phase. This means that they act predominantly as an inert diluent which passes substantially unchanged through the oxidation and/or ammoxidation process. Such a procedure can, however, only be economical when the paraffinic hydrocarbon leaving the partial oxidation and/or partial ammoxidation of the olefinic hydrocarbon is separated from the desired product and then further used for another purpose, as proposed, for example, in EP-A 731 080. On the other hand, recycling to the cracker would not be very expedient and the secondary components accompanying the paraffinic hydrocarbon would in fact usually interfere with the cracker operation.

As a solution to the problem, it has therefore also been proposed to produce the olefinic hydrocarbon required for the partial oxidation and/or ammoxidation by a partial dehydrogenation and/or oxydehydrogenation of a paraffinic hydrocarbon, to separate, if necessary, a portion or the total amount of the components other than the olefinic hydrocarbon present and the remaining paraffinic hydrocarbon from the product mixture and then to use it, containing the olefinic hydrocarbon accompanied by the remaining paraffinic hydrocarbon, for feeding a partial oxidation and/or ammoxidation of the olefinic hydrocarbon. Desired product is then separated from the product mixture of the partial oxidation and/or ammoxidation, and the paraffinic hydrocarbon contained in this product mixture is then recycled at least partly, as paraffinic recycle hydrocarbon, to the dehydrogenation and/or oxydehydrogenation.

The disadvantage of such a procedure is, however, that a dehydrogenation and/or oxydehydrogenation of paraffinic hydrocarbons is as a rule always associated with the production of carbon deposits, which have to be removed from time to time. In order to avoid the necessity of also stopping the partial oxidation and/or ammoxidation in such nonoperating phases, the dehydrogenation and/or oxydehydrogenation is usually carried out using at least two dehydrogenation and/or oxydehydrogenation reactors (which together form a dehydrogenation and/or oxydehydrogenation zone) whose nonoperating phases are staggered in time.

The disadvantage of such a design variant is, however, that it requires investment in at least two dehydrogenation and/or oxydehydrogenation reactors, with the result that the overall cost-efficiency becomes questionable.

However, partial oxidations and/or ammoxidations of olefinic hydrocarbons are now operated at many locations, the olefinic hydrocarbon originating from another source, as a rule one which also supplies further customers.

PCT/EP/01/06528 proposes, particularly for such a setup, implementing a dehydrogenation and/or oxydehydrogenation as described above as a source of the required olefinic hydrocarbon for the normal operation of the partial oxidation and/or ammoxidation of the olefinic hydrocarbon and, during the nonoperating phase of at least a part of this zone, covering the loss of production of olefinic hydrocarbon from the conventional source. Such a procedure would make it possible to minimize the reactor demand for the dehydrogenation and/or oxydehydrogenation zone. However, the disadvantage of such a procedure is that an olefinic hydrocarbon originating from the conventional sources generally has a substantially lower proportion of paraffinic hydrocarbon than an olefinic hydrocarbon originating from the dehydrogenation and/or oxydehydrogenation zone described above.

As a consequence of this, the plant for partial oxidation and/or ammoxidation (including the plant for working up its product mixture) would constantly depart from its normal steady-state operating point to a substantial extent during the nonoperating phase of at least a part of the dehydrogenation and/or oxydehydrogenation zone, which would require additional costs with respect to regulations.

It is an object of the present invention to provide a procedure which has said disadvantage to a lesser extent, if at all. According to the invention, it has now been found that it is possible, for example, if from the beginning of the nonoperating phase of at least part of the dehydrogenation and/or oxydehydrogenation zone, the paraffinic recycle hydrocarbon intended for this part is at least partly not recycled via the dehydrogenation and/or oxydehydrogenation zone to the oxidation and/or ammoxidation zone and subsequently, within the nonoperating phase, is thus constantly fed in this small recycle loop. Of course, it would also be possible, from the beginning of the nonoperating phase, to remove a part of the paraffinic recycle hydrocarbon intended for the nonoperating part of the dehydrogenation and/or oxydehydrogenation zone initially through an outlet and in its place to feed a corresponding fresh amount of paraffinic hydrocarbon to the oxidation and/or ammoxidation zone, which fresh amount is subsequently at least partly fed in the small loop.

SUMMARY OF THE INVENTION

We have found that this object is achieved by a process for the preparation of partial oxidation products and/or partial ammoxidation products of at least one olefinic hydrocarbon A', in which A) in a first reaction zone A, at least one paraffinic hydrocarbon A is subjected to a partial dehydrogenation and/or oxydehydrogenation with formation of a product mixture A which contains an unconverted amount of at least one paraffinic hydrocarbon A and at least one olefinic hydrocarbon A' formed by the partial dehydrogenation and/or oxydehydrogenation, B) a portion or the total amount of the components contained in the product mixture A and differing from the at least one paraffinic hydrocarbon A and the at least one olefinic hydrocarbon A' is separated from said product mixture A, if required a [sic] in a (first) separation zone (separation apparatus), to give a product mixture A', and either the product mixture A or the product mixture A' is used for feeding an oxidation and/or ammoxidation zone B and, in the oxidation and/or ammoxidation zone B, at least the at least one olefinic hydrocarbon A' is subjected to a partial oxidation and/or ammoxidation with formation of a product mixture B which contains, as desired product, at least one partial oxidation and/or ammoxidation product B of the at least one olefinic hydrocarbon A', C) the desired product is separated from the product mixture B in a working-up zone C and at least a portion of the unconverted at least one paraffinic hydrocarbon A contained in the product mixture B is recycled as recycle hydrocarbon A (as part of a recycle stream) into the reaction zone A and D) from time to time, in a nonoperating phase, at least a part of the reaction zone A is not operated for the purpose of the partial dehydrogenation and/or oxydehydrogenation of the at least one paraffinic hydrocarbon A, wherein, during the nonoperating phase of the at least one part of the reaction zone A, the oxidation and/or ammoxidation zone B is further operated and that production loss of the at least one olefinic hydrocarbon A' which is associated with the nonoperating phase is at least partly compensated by feeding at least one olefinic hydrocarbon A' originating from a source other than the reaction zone A and, if required, one or more paraffinic hydrocarbons A originating from a source other than the reaction zone A (a preparation without such a supply of fresh paraffinic hydrocarbon A is preferred) to the oxidation and/or ammoxidation zone B and then recycling at least a portion of the at least one paraffinic hydrocarbon A (as a component of the recycle stream) present in the product mixture B of the oxidation and/or ammoxidation zone B, as paraffinic recycle hydrocarbon A, not via the reaction zone A (i.e. with exclusion of the reaction zone A), into the oxidation and/or ammoxidation zone B. This means that the last-mentioned recycling is carried out, according to the invention, in such a way that no dehydrogenation and/or oxydehydrogenation is passed through along the return path.

If, between the reaction zone A and the reaction zone B, a portion or the total amount of the component contained in the product mixture A and differing from the at least one paraffinic hydrocarbon A and the at least one olefinic hydrocarbon A' is separated from said product mixture A in a separation apparatus (separation zone), in the novel process the at least one olefinic hydrocarbon A' originating from a source other than the reaction zone A is preferably fed in such a way that it passes through the separation apparatus (separation zone).

Moreover, it is preferable in this case to recycle the portion of the paraffinic recycle hydrocarbon A which is not recycled via the reaction zone A to the reaction zone B (as a component of the recycle stream) into the reaction zone B in a manner such that it passes through the abovementioned separation apparatus (separation zone).

DETAILED DESCRIPTION OF THE INVENTION

According to the invention, the reaction zone A may comprise two, three, four or more individual reactors for the partial dehydrogenation and/or oxydehydrogenation.

According to the invention, the reaction zone A preferably comprises only one reactor for the partial dehydrogenation and/or oxydehydrogenation.

Furthermore, the novel process is preferably carried out in such a way that, from the beginning of the nonoperating phase of the at least one part of the reaction zone A, at least a half, preferably at least 75%, very particularly preferably all, of that proportion of the at least one paraffinic recycle hydrocarbon A which is intended for said part of the reaction zone A is no longer recycled via the reaction zone A to the oxidation and/or ammoxidation zone B. Since this proportion of the at least one paraffinic recycle hydrocarbon A is substantially inert with respect to the partial oxidation and/or ammoxidation of the at least one olefinic hydrocarbon A', it remains substantially unchanged during the partial oxidation and/or ammoxidation and can therefore be fed in this small loop (the large loop leads via the reaction zone A) until the nonoperating phase of the at least one part of the reaction zone A has ended. In this way, it is possible to maintain substantially completely unchanged the operating state of the partial oxidation and/or ammoxidation, including the required working-up for isolation of the at least one desired product during the nonoperating phase of the at least one part of the reaction zone A.

According to the invention, desired product is thus isolated from the product mixture B in a working-up zone C, a residual product B being obtained (as a rule, the total amount of desired product is isolated). Secondary components contained in the residual product B and differing from the at least one paraffinic hydrocarbon A can then be partly or completely separated from the residual product mixture B, if required in a (further, a second) separation zone (separation stage), a residual product B containing the at least one paraffinic hydrocarbon A being obtained, and thus, during normal operation (i.e. in the absence of a nonoperating phase), either the residual product mixture B as such or the residual product mixture B' can be recycled to the reaction zone A as recycle stream containing at least one paraffinic recycle hydrocarbon A (according to the invention, preferably only the first or the second separation zone is used; preferably, only the first separation zone is used). In comparison, according to the invention, either the residual product mixture B or the residual product mixture B' is then recycled during the nonoperating phase, as recycle stream containing at least one paraffinic recycle hydrocarbon A, at least partly (preferably completely) with exclusion (with bypassing) of the reaction zone A, into the oxidation and/or ammoxidation zone B. This recycling is preferably effected via the first separation zone if such a zone is used.

This means that, if the reaction zone A for carrying out the novel process comprises only one reactor A for the partial dehydrogenation and/or oxydehydrogenation, the novel process is expediently carried out as follows:

In the reactor A, at least one paraffinic hydrocarbon A is subjected to a partial dehydrogenation and/or oxydehydrogenation, resulting in a product mixture A which contains an unconverted amount of the at least one paraffinic hydrocarbon A and at least one olefinic hydrocarbon A' formed by the partial dehydrogenation and/or oxydehydrogenation.

A portion or the total amount of the components contained in the product mixture A and differing from the at least one paraffinic hydrocarbon A and the at least one olefinic hydrocarbon A' is then separated from said product mixture A, if required in a (first) separation apparatus (separation zone), to give a product mixture A', and then either the product mixture A or the product mixture A' is used for feeding an oxidation and/or ammoxidation zone B.

Usually (and this applies very generally to the novel procedure), the feed mixture A" of the oxidation and/or ammoxidation zone B comprises not only the product mixture A or A'. Rather, additional components, for example oxidizing agents, ammonia, inert diluents, etc., are usually introduced into the product mixture A or A' for producing the feed mixture A". Of course, additional olefinic and/or paraffinic hydrocarbons A' and A, respectively, from sources other than the reaction zone A can be introduced into the feed mixture A" in order to produce a particularly preferred composition of the feed mixture A".

In the oxidation and/or ammoxidation zone B (reaction zone B), the at least one olefinic hydrocarbon A' present in the feed mixture A" is then partially oxidized and/or ammoxidized, a product mixture B being obtained. The product mixture B contains, as at least one desired product, at least one partial oxidation and/or ammoxidation product B of the at least one olefinic hydrocarbon A' and the unconverted at least one paraffinic hydrocarbon A.

In a working-up zone C, desired product is then separated from the product mixture B and thereafter at least a portion (preferably at least half, particularly preferably at least 75%, very particularly preferably the total amount) of the unconverted at least one paraffinic hydrocarbon A (recycle hydrocarbon A) contained in the product mixture B is recycled, as a component of a recycle stream R, into the reactor A.

Of course, the recycle stream R may also contain other components in addition to the at least one paraffinic recycle hydrocarbon A. For example, byproducts from the partial oxydehydrogenation and/or dehydrogenation, byproducts from the partial oxidation and/or ammoxidation, incompletely consumed oxidizing agent, any desired product remaining because of incomplete isolation and any unconverted amounts of the at least one olefinic hydrocarbon A' and impurities of the raw materials used may occur as these other components (secondary components).

Of course, these secondary components can, if required, be also partly or substantially completely separated (in a second separation zone) from the recycle stream R before it is recycled into the reactor A. The recycle stream R is then supplemented by a fresh amount of the at least one paraffinic hydrocarbon A and, if required, further components required for the dehydrogenation and/or oxydehydrogenation and passes again through the production circulation.

If from any point in time the reactor A is no longer operated for a certain period for the purpose of dehydrogenation, according to the invention, from this point in time and for this period, the paraffinic recycle hydrocarbon A would no longer be recycled as part of the recycle stream R into the reaction zone A but at least a part, preferably at least half, more preferably at least 75%, particularly preferably all, of it will be recycled, along a path not leading via the reaction zone A (not leading via a dehydrogenation and/or oxydehydrogenation), into the oxidation and/or ammoxidation zone B (as a component of its feed mixture A"). For example, the recycling of the paraffinic recycle hydrocarbon A (as a component of the recycle stream R) can then be effected substantially directly into the oxidation and/or ammoxidation zone B (reaction zone B) (into the feed mixture A").

If at least a part of the components differing from the at least one olefinic hydrocarbon A' and the remaining at least one paraffinic hydrocarbon A is separated from the product mixture A in a (first) separation apparatus (separation zone) at times when the reactor A is operated for the purpose of the dehydrogenation and/or oxydehydrogenation, before said part of said components is used as product mixture A' for feeding the reaction zone B, that portion of the recycle hydrocarbon A (of the recycle stream R) which is not recycled via the reactor A into the reaction zone B is advantageously recycled, in the period in which the reactor A is not operated for the purpose of the dehydrogenation and/or oxydehydrogenation, into the reaction zone B so that it passes through the (first) separation apparatus (separation zone).

At least a part, preferably at least half, more preferably at least 75%, particularly preferably all, of the at least one olefinic hydrocarbon A' required for the feed mixture A" would be obtained, in said period, from a source other than the reactor A and would be fed to the reaction zone B.

In the abovementioned case, it is preferred according to the invention to effect the feed of the at least one olefinic hydrocarbon A' originating from a source other than the reactor A in such a way that said olefinic hydrocarbon likewise passes through the (first) separation apparatus.

If the at least one olefinic hydrocarbon A' is propylene and the at least one paraffinic hydrocarbon is propane, for example, commercially available cracker propylene having the following purities is available as another such source:

a) Polymer Grade Propylene:
   $\geq 99.6\%$ by weight of propene,
   $\leq 0.4\%$ by weight of propane,
   $\leq 300$ ppm by weight of ethane and/or methane,
   $\leq 5$ ppm by weight of $C_4$-hydrocarbons,
   $\leq 1$ ppm by weight of acetylene,
   $\leq 7$ ppm by weight of ethylene,
   $\leq 5$ ppm by weight of water,
   $\leq 2$ ppm by weight of $O_2$,
   $\leq 2$ ppm by weight of sulfur-containing compounds (calculated as sulfur),
   $\leq 1$ ppm by weight of chlorine-containing compounds (calculated as chlorine),
   $\leq 5$ ppm by weight of $CO_2$,
   $\leq 5$ ppm by weight of CO,
   $\leq 10$ ppm by weight of cyclopropane,
   $\leq 5$ ppm by weight of propadiene and/or propyne,
   $\leq 10$ ppm by weight of $C_{\geq 5}$-hydrocarbon and
   $\leq 10$ ppm by weight of carbonyl-containing compounds (calculated as $Ni(CO)_4$);

b) Chemical-Grade Propylene:
   $\geq 94\%$ by weight of propene
   $\leq 6\%$ by weight of propane,
   $\leq 0.2\%$ by weight of methane and/or ethane,
   $\leq 5$ ppm by weight of ethylene,
   $\leq 1$ ppm by weight of acetylene,
   $\leq 20$ ppm by weight of propadiene and/or propyne,
   $\leq 100$ ppm by weight of cyclopropane,
   $\leq 50$ ppm by weight of butene,
   $\leq 50$ ppm by weight of butadiene,
   $\leq 200$ ppm by weight of $C_4$-hydrocarbons,
   $\leq 10$ ppm by weight of $C_{\geq 5}$-hydrocarbons,
   $\leq 2$ ppm by weight of sulfur-containing compounds (calculated as sulfur),
   $\leq 0.1$ ppm by weight of sulfides (calculated as $H_2S$),
   $\leq 1$ ppm by weight of chlorine-containing compounds (calculated as chlorine),
   $\leq 1$ ppm by weight of chloride (calculated as $Cl\ominus$) and
   $\leq 30$ ppm by weight of water.

The composition of the feed mixture A" and hence the operating state of the oxidation and/or ammoxidation zone B and of the working-up zone C can thus be maintained substantially unchanged in the manner described, even during an interruption to the dehydrogenation and/or oxydehydrogenation in the reactor A, without excessively high capital costs.

In the novel process, the at least one paraffinic hydrocarbon A is preferably ethane, propane, n-butane and/or isobutane. Its purity does not have to meet any particular requirements.

The partial dehydrogenation and/or oxydehydrogenation of the at least one paraffinic hydrocarbon A can be carried out in a manner known per se to a person skilled in the art, as described, for example, in DE-A 19 837 517, DE-A 19 837 519, DE-A 19 837 520, EP-A 117 146, DE-A 3 313 573, U.S. Pat. No. 3,161,670, DE-A 10028582, PCT/EP/01/06708, EP-A 328 280, EP-A 193 310, EP-A 372 972 and U.S. Pat. No. 4,849,538, in the case of propane. It can be carried out as a homogeneous and/or heterogeneously catalyzed oxydehydrogenation and as a heterogeneously catalyzed dehydrogenation. Usually, it is carried out at elevated temperatures in the gas phase. In a corresponding manner, the partial oxidation and/or ammoxidation of the at least one paraffinic hydrocarbon A can be carried out in a manner known to a person skilled in the art.

Usually, it is likewise carried out in the gas phase as a heterogeneously catalyzed partial oxidation and/or ammoxidation, the catalysts used being solid multimetal oxides. Specific embodiments are also to be found in the prior art referred to above with regard to carrying out the partial dehydrogenation and/or oxydehydrogenation.

In particular acrolein, acrylic acid, methacrolein, methacrylic acid, maleic anhydride, acrylonitrile, methacrylonitrile, vinyloxirane, propylene oxide and ethylene oxide are of interest as desired products for the novel procedure.

Their separation from the product mixture B can be effected in the working-up zone C, likewise in a manner known per se to a person skilled in the art. Further details in this respect are likewise to be found in the prior art referred to above with regard to carrying out the partial dehydrogenation and/or oxydehydrogenation.

Expediently, substantially only one paraffinic hydrocarbon A is dehydrogenated and/or oxydehydrogenated in the reaction zone A in the novel process. This is possible in particular when a crude paraffinic hydrocarbon A which contains substantially no other paraffinic hydrocarbons is used for this purpose.

Some particular possible embodiments of the novel process are explained below using a novel preparation of acrolein and/or acrylic acid starting from propane by way of example. They are applicable in an analogous manner to the other novel processes stated in this document and can be used in an analogous manner for said processes.

In the case of an oxydehydrogenation of propane, this can be carried out as a homogeneous and/or heterogeneously catalyzed oxydehydrogenation of propane to propene with molecular oxygen in the gas phase. Air, pure molecular oxygen or air enriched in molecular oxygen can be used as a source of the molecular oxygen.

If the reaction zone A is designed as a homogeneous oxydehydrogenation, this can be carried out in principle as described, for example, in U.S. Pat. No. 3,798,283, CN-A 1 105 352, Applied Catalysis, 70(2) (1991), 175-187, Catalysis Today 13, (1992), 673-678 and DE-A 19 622 331. An expedient oxygen source is air. The temperature of the homogeneous oxydehydrogenation is expediently chosen to be in the range from 300 to 700° C., preferably from 400 to 600° C., particularly preferably from 400 to 500° C. The operating pressure may be from 0.5 to 100, in particular from 1 to 10, bar. The residence time is usually from 0.1 or 0.5 to 20, preferably from 0.1 or 0.5 to 5, seconds.

The reactor used may be, for example, a tubular reactor or a tube-bundle reactor, for example a countercurrent tubular oven with stack gas as a heating medium or a tube-bundle reactor with salt melt as a heating medium. The propane-to-oxygen ratio in the starting mixture is preferably from 0.5:1 to 40:1, in particular from 1:1 to 6:1, particularly preferably from 2:1 to 5:1. The starting mixture may also comprise further, substantially inert, components, such as water, carbon dioxide, carbon monoxide, nitrogen, noble gases and/or propene, it also being possible for these to be recycled components.

If the propane dehydrogenation is designed as a heterogeneously catalyzed oxydehydrogenation, this can be carried out in principle as described, for example, in U.S. Pat. No. 4,788,371, CN-A 1073893, Catalysis Letters 23 (1994), 103-106, W. Zhang, Gaodeng Xuexiao Huaxue Xuebao, 14 (1993), 566, Z. Huang, Shiyou Huagong, 21 (1992), 592, WO 97/36849, DE-A 197 53 817, U.S. Pat. No. 3,862,256, U.S. Pat. No. 3,887,631, DE-A 195 30 454, U.S. Pat. No. 4,341,664, J. of Catalysis 167 (1997), 560-569, J. of Catalysis 167 (1997), 550-559, Topics in Catalysis 3 (1996), 265-275, U.S. Pat. No. 5,086,032, Catalysis Letters 10 (1991), 181-192, Ind. Eng. Chem. Res. 35 (1996), 14-18, U.S. Pat. No. 4,255,284, Applied Catalysis A: General, 100 (1993), 111-130, J. of Catalysis 148 (1994), 56-67, V. Cortés Corberán and S. Vic Bellón (Ed.), New Developments in Selective Oxidation II, 1994, Elsevier Science B. V., pages 305-313, 3rd World Congress on Oxidation Catalysis, R. K. Grasselli, S. T. Oyama, A. M. Gaffney and J. E. Lyons (Ed.), 1997, Elsevier Science B. V., page 375 et seq. Air may also be used as the oxygen source. Frequently, however, the oxygen source here comprises at least 90 mol % of molecular oxygen, often at least 95 mol % of oxygen.

The catalysts suitable for the heterogeneously catalyzed oxydehydrogenation are not subject to any particular restrictions. All oxydehydrogenation catalysts which are known in this area to a person skilled in the art and which are capable of oxidizing propane to propene are suitable. In particular, all oxydehydrogenation catalysts stated in the abovementioned publications may be used. Suitable catalysts are, for example, oxydehydrogenation catalysts which comprise MoVNb oxides or vanadyl pyrophosphate, in each case with a promoter. An example of an advantageous oxydehydrogenation catalyst is a catalyst which contains a mixed metal oxide with Mo, V, Te, O and X as substantial components, where X is at least one element selected from niobium, tantalum, tungsten, titanium, aluminum, zirconium, chromium, manganese, iron, ruthenium, cobalt, rhodium, nickel, palladium, platinum, antimony, bismuth, boron, indium and cerium. Particularly suitable oxydehydrogenation catalysts are furthermore the multimetal oxide materials or catalysts A of DE-A-197 53 817, the multimetal oxide materials or catalysts A stated as being preferred in the abovementioned publication being very particularly advantageous. This means that in particular multimetal oxide materials (IV) of the formula IV $$M^1{}_a MO_{1-b} M^2{}_b O_x \qquad (IV),$$

where

M$^1$ is CO, Ni, Mg, Zn, Mn and/or Cu,

M$^2$ is W, V, Te, Nb, P, Cr, Fe, Sb, Ce, Sn and/or La, a is 0.5-1.5, b is 0-0.5 and x is a number which is determined by the valency and frequency of the elements other than oxygen in (IV), are suitable as active materials.

In principle, suitable active materials (IV) can be prepared in a simple manner by producing, from suitable sources of their elemental constituents, a very intimate, preferably finely divided dry blend having a composition corresponding to their stoichiometry and calcining said dry blend at from 450 to 1000° C. Suitable sources of the elemental constituents of the multimetal oxide active materials (IV) are those compounds which are already oxides and/or those compounds which can be converted into oxides by heating, at least in the presence of oxygen. These are in particular halides, nitrates, formates, oxalates, citrates, acetates, carbonates, ammine complex salts, ammonium salts and/or hydroxides. The thorough mixing of the starting compounds for the preparation of the multimetal oxide materials (IV) can be effected in dry form, for example as finely divided powder, or in wet form, for example using water as a solvent. The multimetal oxide materials (IV) can be used both in powder form and after shaping to give specific catalyst geometries, it being possible for the shaping to be effected before or after the final calcination. Unsupported catalysts may be used. However, the shaping of an active material or precursor material in powder form can also be effected by application to premolded inert catalyst supports. Conventional, porous or nonporous aluminas, silica, thorium dioxide, zirconium dioxide, silicon carbide or silicates may be used as support material, it being possible for the supports to have a regular or irregular shape.

For the heterogeneously catalyzed oxydehydrogenation of propane, the reaction temperature is preferably from 200 to 600° C., in particular from 250 to 500° C., particularly preferably from 350 to 440° C. The operating pressure is preferably from 0.5 to 10, in particular from 1 to 10, particularly preferably from 1 to 5, bar. Operating pressures above 1 bar, for example from 1.5 to 10 bar, have proven particularly advantageous. As a rule, the heterogeneously catalyzed oxydehydrogenation of propane is carried out over a fixed catalyst bed. The latter is expediently poured into the tubes of a tube-bundle reactor, as described, for example, in EP-A-0 700 893 and in EP-A-0 700 714 and the literature cited in these publications. The average residence time of the reaction gas mixture in the catalyst bed is expediently from 0.5 to 20 seconds. The ratio of propane to oxygen varies with the desired conversion and the selectivity of the catalyst and is expediently from 0.5:1 to 40:1, in particular from 1:1 to 6:1, particularly preferably from 2:1 to 5:1. As a rule, the propene selectivity decreases with increasing propane conversion. The propane-to-propene reaction is therefore preferably carried out in such a way that relatively low conversions of propane in combination with high selectivities with respect to propene are achieved. The propane conversion is particularly preferably from 5 to 40, frequently from 10 to 30, mol %. Here, the term propane conversion means the proportion of propane fed in which is converted in a single pass. As a rule, the selectivity of the propane formation is from 50 to 98, particularly preferably from 80 to 98, mol %, the term selectivity referring to the number of moles of propene which are produced per mole of propane converted, expressed as a molar percentage.

As a rule, the starting mixture used in the oxidative propane dehydrogenation contains from 5 to 95 mol % of propane (based on 100 mol % of starting mixture). In addition to propane and oxygen, the starting mixture for the heterogeneously catalyzed oxydehydrogenation may also comprise further, in particular inert, components, such as carbon dioxide, carbon monoxide, nitrogen, noble gases and/or propene. The heterogeneous oxydehydrogenation can also be carried out in the presence of diluents, for example steam.

Any desired reactor sequence which is known to a person skilled in the art can be used for carrying out the homogeneous oxydehydrogenation or the heterogeneously catalyzed oxydehydrogenation of propane. For example, the oxydehydrogenation can be carried out in a single reactor or in a cascade of two or more reactors, between which, if required, oxygen is introduced. It is also possible to implement the homogeneous and heterogeneously catalyzed oxydehydrogenation in combination with one another.

The product mixture of a propane oxydehydrogenation may contain, for example, the following components as possible constituents: propene, propane, carbon dioxide, carbon monoxide, water, nitrogen, oxygen, ethane, ethene, methane, acrolein, acrylic acid, ethylene oxide, butane, acetic acid, formaldehyde, formic acid, propylene oxide and butene. Typically, a product mixture obtained in the propane oxydehydrogenation contains: from 5 to 10 mol % of propene, from 1 to 2 mol % of carbon monoxide, from 1 to 3 mol % of carbon dioxide, from 4 to 10 mol % of water, from 0 to 1 mol % of nitrogen, from 0.1 to 0.5 mol % of acrolein, from 0 to 1 mol % of acrylic acid, from 0.05 to 0.2 mol % of acetic acid, from 0.01 to 0.05 mol % of formaldehyde, from 1 to 5 mol % of oxygen, from 0.1 to 1.0 mol % of further abovementioned components and, as the remainder, substantially propane, based in each case on 100 mol % of product mixture.

In general, the propane dehydrogenation in the reaction zone A can also be carried out as a heterogeneously catalyzed propane dehydrogenation with substantial exclusion of oxygen, as described in DE-A 33 13 573, or as follows.

Since the heterogeneously catalyzed dehydrogenation reaction takes place with an increase in volume, the conversion can be increased by reducing the partial pressure of the products. This can be achieved in a simple manner, for example by dehydrogenation at reduced pressure and/or by admixing substantially inert diluent gases, for example steam, which is usually an inert gas for the dehydrogenation reaction. Dilution with steam generally results, as a further advantage, in reduced coking of the catalyst used, since the steam reacts with coke formed according to the principle of coal gasification. Moreover, steam can be concomitantly used as diluent gas in the downstream oxidation and/or ammoxidation zone B (also reaction zone B for short in this document). However, steam can also be partly or completely separated from the product mixture A in a simple manner (for example by condensation), which makes it possible to increase the proportion of the diluent gas $N_2$ when the product gas mixture A' obtainable is further used in the reaction zone B. Other diluents suitable for the heterogeneously catalyzed propane dehydrogenation are, for example, CO, methane, ethane, $CO_2$, nitrogen and noble gases, such as He, Ne and Ar. All diluents mentioned can be concomitantly used either by themselves or in the form of a wide range of mixtures. It is advantageous that said diluents are as a rule also suitable diluents in the reaction zone B. In general, diluents which are inert (i.e. undergo chemical change to an extent of less than 5, preferably less than 3, particularly preferably less than 1, mol %) in the respective stage are preferred. In principle, all dehydrogenation catalysts known in the prior art are suitable for the heterogeneously catalyzed propane dehydrogenation. They may be divided generally into two groups, i.e. into those which are of an oxidic nature (for example chromium oxide and/or alumina) and into those which consist of at least one, as a rule comparatively noble, metal (for example platinum) deposited on a generally oxidic support.

Inter alia, all dehydrogenation catalysts which are recommended in WO 99/46039, U.S. Pat. No. 4,788,371, EP-A-0 705 136, WO 99/29420, U.S. Pat. No. 4,220,091, U.S. Pat. No. 5,430,220, U.S. Pat. No. 5,877,369, EP-A-0 117 146, DE-A 199 37 196, DE-A 199 37 105 and DE-A 199 37 107 can thus be used. In particular, the catalysts according to example 1, example 2, example 3 and example 4 of DE-A 199 37 107 can be used.

These are dehydrogenation catalysts which contain from 10 to 99.9% by weight of zirconium dioxide, from 0 to 60% by weight of alumina, silica and/or titanium dioxide and from 0.1 to 10% by weight of at least one element of the first or second main group, one element of the third subgroup, one element of the eighth subgroup of the Periodic Table of the Elements, lanthanum and/or tin, with the proviso that the sum of the percentage by weight is 100% by weight.

In principle, all reactor types and process variants known in the prior art are suitable for carrying out the heterogeneously catalyzed propane dehydrogenation. Descriptions of such process variants are contained, for example, in all prior art publications cited in relation to the dehydrogenation catalysts.

A comparatively detailed description of dehydrogenation processes suitable according to the invention is also contained in Catalytica® Studies Division, Oxidative Dehydrogenation and Alternative Dehydrogenation Processes, Study Number 4192 OD, 1993, 430 Ferguson Drive, Mountain View, Calif., 94043-5272 U.S.A.

Typical of partial heterogeneously catalyzed dehydrogenation of propane is that it takes place endothermically. This means that the heat (energy) necessary for establishing the required reaction temperature must be supplied either before the reaction gas starting mixture and/or in the course of the heterogeneously catalyzed dehydrogenation.

Furthermore, owing to the high reaction temperatures required, it is typical in particular for heterogeneously catalyzed dehydrogenations of propane that small amounts of high-boiling high molecular weight organic compounds, including carbon, are formed, which compounds are deposited on the catalyst surface and thus deactivate it. In order to minimize this disadvantageous accompanying phenomenon, the propane-containing reaction mixture to be passed over the catalyst surface for the heterogeneously catalyzed dehydrogenation at elevated temperatures can be diluted with steam. Under the resulting conditions, any carbon deposited is partly or completely eliminated according to the principle of coal gasification.

Another possibility for eliminating deposited carbon compounds is to pass an oxygen-containing gas through the dehydrogenation catalyst from time to time at elevated temperatures and thus virtually to burn off the deposited carbon. Substantial suppression of the formation of carbon deposits is, however, also possible by adding molecular hydrogen to the propane to be dehydrogenated under heterogeneous catalysis before it is passed over the dehydrogenation catalyst at elevated temperatures.

Of course, it is also possible to add steam and molecular hydrogen as a mixture to the propane to be dehydrogenated under heterogeneous catalysis. An addition of molecular hydrogen for the heterogeneously catalyzed dehydrogenation of propane also reduces the undesired formation of allene and acetylene as byproducts.

A suitable reactor form for the heterogeneously catalyzed propane dehydrogenation is a fixed-bed tubular reactor or tube-bundle reactor. This means that the dehydrogenation catalyst is present as a fixed bed in a reaction tube or in a bundle of reaction tubes. The reaction tubes are heated by combustion of a gas, for example a hydrocarbon, such as methane, in the space surrounding the reaction tubes. It is advantageous to apply this direct form of catalyst tube heating only to about the first 20 to 30% of the fixed bed and to heat the remaining bed length to the required reaction temperature by the radiant heat liberated in the course of the combustion. In this way, a virtually isothermal reaction is achievable. Suitable internal diameters of reaction tubes are from about 10 to 15 cm. A typical dehydrogenation tube-bundle reactor comprises from 300 to 1 000 reaction tubes. The temperature in the interior of the reaction tubes is from 300 to 700° C., preferably from 400 to 700° C. The reaction gas starting mixture is advantageously preheated to the reaction temperature before being fed to the tubular reactor. Frequently, the product gas mixture leaves the reaction tube at a temperature which is from 50 to 100° C. lower. In the abovementioned procedure, the use of oxidic dehydrogenation catalysts based on chromium oxide and/or alumina is expedient. Frequently, no diluent gas is present and instead substantially pure propane is used as a starting reaction gas. The dehydrogenation catalyst, too, is generally used in undiluted form.

On an industrial scale, a plurality of such tube-bundle reactors (for example three) can be operated in parallel. According to the invention, two of these reactors may be present in the dehydrogenation mode while the catalyst load is being regenerated in a third reactor, without the operation in the reaction zone B suffering.

Such a procedure is expedient, for example, in the BASF-Linde propane dehydrogenation process known in the literature. What is important according to the invention, however, is that the use of such a tube-bundle reactor is sufficient.

Such a procedure can also be used in the steam active reforming (STAR) process developed by Phillips Petroleum Co. (cf. for example U.S. Pat. Nos. 4,902,849, 4,996,387 and 5,389,342). Promoter-containing platinum on zinc (magnesium) spinel as a support is advantageously used as a dehydrogenation catalyst in the STAR process (cf. for example U.S. Pat. No. 5,073,662). In contrast to the BASF Linde propane dehydrogenation process, the propane to be dehydrogenated is diluted with steam in the STAR process. A molar ratio of steam to propane of from 4 to 6 is typical. The operating pressure is frequently from 3 to 8 atm and the reaction temperature is expediently chosen to be from 480 to 620° C. Typical catalyst space velocities with the total reaction gas mixture are from 0.5 to 10 h$^{-1}$ (LHSV).

The heterogeneously catalyzed propane dehydrogenation can also be effected in a moving bed. For example, the moving catalyst bed can be housed in a radial-flow reactor. The catalyst moves slowly therein from top to bottom while the reaction gas mixture flows radially. This procedure is used, for example, in the UOP Oleflex dehydrogenation process. Since the reactors in this process are operated quasiadiabatically, it is expedient to operate a plurality of reactors connected in series as cascades (typically up to four). This makes it possible to avoid excessively large differences between the temperatures of the reaction gas mixture at the reactor entrance and at the reactor exit (in the case of adiabatic mode of operation, the reaction gas starting mixture acts as a heating medium, on the heat content of which the drop in the reaction temperature is dependent) and nevertheless achieve attractive total conversions.

When the catalyst bed has left the moving bed reactor, it is fed for regeneration and then reused. For example, a spherical dehydrogenation catalyst which substantially comprises platinum on a spherical alumina support can be used as a dehydrogenation catalyst for this process. In the UOP variant, hydrogen is added to the propane to be dehydrogenated, in order to avoid premature catalyst aging. The operating pressure is typically from 2 to 5 atm. The molar hydrogen-to-propane ratio is expediently from 0.1 to 1. The reaction temperatures are preferably from 550 to 650° C. and the contact time of the catalyst with reaction gas mixture is chosen to be from about 2 to 6 h$^{-1}$.

In the fixed-bed process described, the catalyst may likewise have a spherical geometry but may also be cylindrical (hollow or solid) or have another geometry.

Proceedings de Witt, Petrochem. Review, Houston, Tex., 1992 a, N1, describes the possibility of a heterogeneously catalyzed propane dehydrogenation in a fluidized bed, in which the propane is not diluted, as a further process variant for the heterogeneously catalyzed propane dehydrogenation.

According to the invention, for example, two fluidized beds can be operated side by side, one of which may be in the regeneration state from time to time without any adverse effects on the overall process. The active material used here is chromium oxide on alumina. The operating pressure is typically from 1 to 1.5 atm and the dehydrogenation temperature is as a rule from 550 to 600° C. The heat required for the dehydrogenation is introduced into the reactor by preheating the dehydrogenation catalyst to the reaction temperature. The operating pressure is usually from 1 to 2 atm and the reaction temperature is typically from 550 to 600° C. The above dehydrogenation procedure is also known in the literature as the Snamprogetti-Yarsintez process.

As an alternative to the procedures described above, the heterogeneously catalyzed propane dehydrogenation with substantial exclusion of oxygen can also be realized by a process developed by ABB Lummus Crest (cf. Proceedings De Witt, Petrochem. Review, Houston, Tex., 1992, P1).

A common aspect of the process described to date for the heterogeneously catalyzed dehydrogenation of propane with substantial exclusion of oxygen is that they are operated at propane conversions of >30 mol % (as a rule ≦60 mol %) (based on a single pass through the reaction zone). What is advantageous according to the invention is that it is sufficient to obtain a propane conversion of from ≧5 mol % to ≦30 mol % or ≧25 mol %. This means that the heterogeneously catalyzed propane dehydrogenation can also be operated at propane conversions of from 10 to 20 mol % (the conversions relate to a single pass through the reaction zone). This is because, inter alia, the remaining amount of unconverted propane in the downstream reaction zone B acts as inert diluent gas and can subsequently be recycled substantially without loss into the reaction zone.

For realizing the abovementioned propane conversions, it is advantageous to carry out the heterogeneously catalyzed propane dehydrogenation at an operating pressure of from 0.3 to 3 atm. Furthermore, it is advantageous if the propane dehydrogenated under heterogeneous catalysis is diluted with steam. In this way, first the heat capacity of the water enables a part of the effect of the endothermic nature of the dehydrogenation to be compensated and secondly the dilution with steam reduces the partial pressure of starting materials and product, which has an advantageous effect on the equilibrium position of the dehydrogenation. Furthermore, as stated above, the presence of steam has an advantageous effect on the time-on-stream of the dehydrogenation catalyst. If required, molecular hydrogen may also be added as further component. The molar ratio of molecular hydrogen to propane is as a rule ≦5. The molar ratio of steam to propane can accordingly expediently be from 0.1 to 2, advantageously from 0.5 to 1, with a comparatively low propane conversion of from ≧0 to 30. What also proves to be advantageous for a procedure having a low propane conversion is that only a comparatively small quantity of heat is consumed in a single reactor pass of the reaction gas and comparatively low reaction temperatures are sufficient for achieving the conversion in a single reactor pass.

It may therefore be expedient if the propane dehydrogenation with comparatively low propane conversion is carried out (quasi)adiabatically. This means that the reaction gas starting mixture is as a rule first heated to a temperature of from 500 to 700° C. (or from 550 to 650° C.) (for example by direct firing of the wall surrounding it). Usually, a single adiabatic pass through a catalyst bed is then sufficient to achieve the desired conversion, the reaction gas mixture being cooled by from about 30° C. to 200° C. (depending on conversion). The presence of steam as a heating medium is advantageous also from the point of view of an adiabatic procedure. The low reaction temperature permits longer times-on-stream of the catalyst bed used.

In principle, the heterogeneously catalyzed propane dehydrogenation with comparatively low propane conversion, whether carried out adiabatically or isothermally, can be effected both in a fixed-bed reactor and in a moving-bed or fluidized-bed reactor.

It is noteworthy that, in the novel process, particularly in adiabatic operation, a single shaft reactor is sufficient as a fixed-bed reactor through which the reaction gas mixture flows axially and/or radially.

In the simplest case, this is a single closed reaction volume, for example a container whose internal diameter is from 0.1 to 10 m, possibly also from 0.5 to 5 m, and in which the fixed catalyst bed is applied to a support apparatus (for example a grid). The hot, propane-containing reaction gas flows axially through the reaction volume loaded with catalyst and is heat-insulated in adiabatic operation. The catalyst geometry can be both spherical and annular or strand-like. Since in this case the reaction volume can be realized by a very economical apparatus, all catalyst geometries which have a particularly low pressure drop are preferred. These are in particular catalyst geometries which lead to a large cavity volume or are structured, for example monoliths or honeycomb elements. In order to realize a radial flow of the propane-containing reaction gas, the reactor may consist, for example, of two cylindrical grids present in a shell and positioned concentrically one inside the other and the catalyst bed may be arranged in their annular gap. In the adiabatic case, the metal shell would in turn be thermally insulated.

The catalysts disclosed in DE-A 199 37 107, especially all those disclosed by way of example, are particularly suitable as a catalyst load for the heterogeneously catalyzed propane dehydrogenation with comparatively low propane conversion in a single pass.

After prolonged operation, abovementioned catalysts can be regenerated, for example, in a simple manner by first passing air diluted with nitrogen over the catalyst bed at from 300 to 600° C., frequently from 400 to 500° C., in first regeneration stages. The catalyst space velocity with regeneration gas may be, for example, from 50 to 10 000 h$^{-1}$ and the oxygen content of the regeneration gas may be from 0.5 to 20% by volume.

In downstream further regeneration stages under otherwise identical regeneration conditions, air may be used as regeneration gas. It is expedient in terms of application technology if the catalyst is flushed with inert gas (for example $N_2$) before its regeneration.

Thereafter, it is usually advisable to effect regeneration with pure molecular hydrogen or with molecular hydrogen diluted with inert gas (the hydrogen content should be ≧1% by volume) under otherwise identical conditions.

The heterogeneously catalyzed propane dehydrogenation with comparatively low propane conversion ($\leqq 30$ mol %) can be operated in all cases at the same catalyst space velocities (relating both to the reaction gas as a whole and to the propane contained therein) as the variants with high propane conversion (>30 mol %). This space velocity with reaction gas may be, for example, from 100 to 10 000 h$^{-1}$, frequently from 100 to 3 000 h$^{-1}$, i.e. often from about 100 to 2 000 h$^{-1}$.

The heterogeneously catalyzed propane dehydrogenation with comparatively low propane conversion can be realized in a particularly elegant manner in a tray reactor.

This contains, spatially in succession, more than one catalyst bed catalyzing the dehydrogenation. The number of catalyst beds may be from 1 to 20, expediently from 2 to 8, but also from 3 to 6. The catalyst beds are preferably arranged radially or axially one behind the other. It is expedient in terms of application technology if the fixed catalyst bed type is used in such a tray reactor.

In the simplest case, the fixed catalyst beds are arranged axially in a shaft reactor or in the annular gaps of cylindrical grids positioned concentrically one inside the other. However, it is also possible to arrange the annular gaps in segments one on top of the other and to pass the gas, after it is passed radially through one segment, into the next segment above or below.

Expediently, the reaction gas mixture is subjected to intermediate heating in the tray reactor on its way from one catalyst bed to the next catalyst bed, for example by passing it over heat exchanger ribs heated with hot gases by passing it through tubes heated with hot combustion gases.

If the tray reactor is otherwise operated adiabatically, it is sufficient for the desired propane conversion ($\leqq 30$ mol %), in particular with the use of the catalysts described in DE-A 199 37 107, in particular those of the exemplary embodiments, if the reaction gas mixture is preheated to a temperature of from 450 to 550° C. before being fed into the dehydrogenation reactor and is kept within this temperature range inside the tray reactor. This means that the total propane dehydrogenation should thus be realized at extremely low temperatures, which proves particularly advantageous for the time-on-stream of the fixed catalyst beds between two regenerations.

It is even more elegant to carry out the intermediate heating described above by a direct method (autothermal procedure). For this purpose, a limited amount of molecular oxygen is added to the reaction gas mixture before it flows through the first catalyst bed and/or between the downstream catalyst beds. Depending on the dehydrogenation catalyst used, limited combustion of the hydrocarbons contained in the reaction gas mixture, any carbon or carbon-like compounds deposited on the catalyst surface and/or hydrogen formed in the course of the heterogeneously catalyzed propane dehydrogenation and/or added to the reaction gas mixture is thus effected (it may also be expedient in terms of application technology to introduce into the tray reactor catalyst beds which are loaded with catalyst which specifically (selectively) catalyzes the combustion of hydrogen (and/or of hydrocarbon) (suitable catalysts of this type are, for example, those of U.S. Pat. Nos. 4,788,371, 4,886,928, 5,430,209, 5,530,171, 5,527,979 and 5,563,314; for example, such catalyst beds can be housed in the tray reactor so as to alternate with the beds containing dehydrogenation catalyst). The heat of reaction evolved thus permits virtually isothermal operation of the heterogeneously catalyzed propane dehydrogenation in a quasiautothermal manner. As the chosen residence time of the reaction gas in the catalyst bed increases, a propane dehydrogenation with decreasing or substantially constant temperature is possible, which permits particularly long times-on-stream between two regenerations.

As a rule, an oxygen feed as described above should be effected so that the oxygen content of the reaction gas mixture is from 0.5 to 30% by volume, based on the amount of propane and propene contained therein. Suitable oxygen sources are both pure molecular oxygen and oxygen diluted with inert gas, for example CO, $CO_2$, $N_2$ or noble gases, in particular air. The resulting combustion gases generally have an additional diluting effect and thus promote the heterogeneously catalyzed propane dehydrogenation.

The isothermal nature of the heterogeneously catalyzed propane dehydrogenation can be further improved by mounting closed internals (for example annular ones), advantageously but not necessarily evacuated before the introduction, in the spaces between the catalyst beds in the tray reactor. Such internals may also be placed in the respective catalyst bed. These internals contain suitable solids or liquids which evaporate or melt above a specific temperature and thus consume heat and condense and thereby liberate heat where the temperature falls below this temperature.

One possibility of heating the reaction gas starting mixture for the heterogeneously catalyzed propane dehydrogenation to the reaction temperature required is also to combust a part of the propane and/or $H_2$ contained therein by means of molecular oxygen (for example, over suitable combustion catalysts having a specific action, for example by simply passing over and/or passing through) and to effect heating to the desired reaction temperature by means of the heat of combustion thus liberated. The resulting combustion products, such as $CO_2$ and $H_2O$, and any $N_2$ accompanying the molecular oxygen required for the combustion advantageously form inert diluent gases.

The product gas mixture A formed in the course of the heterogeneously catalyzed propane dehydrogenation contains as a rule propane, propene, molecular hydrogen, $N_2$, $H_2O$, methane, ethane, ethylene, CO and $CO_2$. As a rule, it is present at a pressure of from 0.3 to 10 atm and frequently at a temperature of from 400 to 500° C., in advantageous cases from 450 to 500° C.

While EP-A 117 146, DE-A 3 313 573 and U.S. Pat. No. 3,161,670 recommend using the product gas mixture A formed in the heterogeneously catalyzed propane dehydrogenation as such for feeding the reaction zone B, DE-A 10028582 recommends separating at least a portion of the hydrogen formed during the heterogeneously catalyzed propane dehydrogenation from the product gas mixture A before it is further used for feeding the reaction zone B.

This can be effected, for example, by passing the product gas mixture A, if necessary after it has been cooled beforehand in an indirect heat exchanger (expediently, the heat removed is used for heating a feed gas required for the novel process), over a membrane, which as a rule is formed into a tube and is permeable only to molecular hydrogen. Some of the molecular hydrogen separated off in this manner can, if required, be recycled to the heterogeneously catalyzed dehydrogenation of propane or otherwise utilized. In the simplest case, it can be combusted in fuel cells.

Alternatively, hydrogen can be separated off partially or completely also by partial condensation, adsorption and/or rectification (preferably under pressure). The partial or complete separation of the molecular hydrogen from the product gas mixture A can be carried out in the novel process also by selective (e.g. heterogeneously catalyzed) combustion thereof with molecular oxygen. The resulting water of reaction can either be separated off partly or completely or left in the gas mixture, since it is capable of acting as inert diluent gas in the reaction zone B. Catalysts suitable in this respect are disclosed, for example, in U.S. Pat. Nos. 4,788,371, 4,886,928, 5,430,209, 5,530,171, 5,527,979 and 5,563,314.

The selective combustion of the molecular hydrogen can also be carried out so to speak in situ during the heterogeneously catalyzed dehydrogenation itself, for example by oxidation by means of a reducible metal oxide also added to the dehydrogenation catalyst, as described, for example, in EP-A 832056.

It is expedient according to the invention if at least 10 or at least 25, frequently at least 35 or at least 50, often at least 75, mol % and often the total amount of the molecular hydrogen formed in the course of the heterogeneously catalyzed dehydrogenation is separated off before the remaining product gas mixture A' is used for feeding the reaction zone B. If required, any water present may also be separated (for example condensed) from the product gas mixture A before it is further processed in the reaction zone B. If necessary, removal of other components of the product gas mixture A which differ from propane and propene can of course also be carried out during the removal of molecular hydrogen.

A simple possibility for separating off substantially all components of the product gas mixture A which differ from propane and propene comprises bringing the product gas mixture A which has preferably been cooled (preferably to temperatures of from 10 to 70° C.), for example at from 0.1 to 50 atm and from 0 to 100° C., into contact with a (preferably high-boiling) organic solvent (preferably a hydrophobic one) in which propane and propene are preferably absorbed (for example by simply passing said product gas mixture A through). By subsequent desorption, rectification and/or stripping with a gas inert with respect to the reaction zone B and/or required as a reactant in this reaction zone (e.g. air), the propane and propene in the mixture are recovered in comparatively pure form and used for feeding the reaction zone B. The exit gas of the absorption, which contains the molecular hydrogen can, for example, be subjected to a membrane separation again and then, if required, the hydrogen separated off can be concomitantly used in the heterogeneously catalyzed propane dehydrogenation.

In particular, the removal described above is an excellent basis for eliminating the necessity of using pure propane for the heterogeneously catalyzed propane dehydrogenation. Rather, the propane used may contain up to 50% by volume of other gases, e.g. ethane, methane, ethylene, butanes, butenes, acetylene, $H_2S$, $SO_2$, pentanes, etc., since, after all, the major part of these byproducts is simultaneously separated off in the course of the separation step described. As an alternative to the described separation step by means of absorption, a pressure swing adsorption would also be possible. Expediently, the crude propane to be used contains at least 60, advantageously at least 70, preferably at least 80, particularly preferably at least 90, very particularly preferably at least 95, % by volume of propane. In articular, a mixture of propane, propene and recycle gas originating from the oxidation stage can also be used for the heterogeneously catalyzed propane dehydrogenation.

Suitable absorbents for the separation described above are in rinciple all absorbents which are capable of absorbing propane and propene. The absorbent is preferably an organic solvent which is preferably hydrophobic and/or high-boiling. This solvent advantageously has a boiling point (at an atmospheric pressure of 1 atm) of at least 120° C., preferably at least 180° C., especially from 200 to 350° C., in particular from 250 to 300° C., particularly preferably from 260 to 290° C. The flashpoint (at an atmospheric pressure of 1 atm) is expediently above 110° C. In general, suitable absorbents are relatively nonpolar organic solvents, for example aliphatic hydrocarbons which preferably contain no externally acting polar group, but also aromatic hydrocarbons. In general, it is desirable for the absorbent to have a very high boiling point in combination with very high propane and propene solubilities. Examples of absorbents are aliphatic hydrocarbons, for example $C_8$-$C_{20}$-alkanes or $C_8$-$C_{20}$-alkenes, and aromatic hydrocarbons, for example middle oil fractions from paraffin distillation or ethers having bulky groups on the oxygen atom, and mixtures thereof, it being possible for a polar solvent, for example the 1,2-dimethyl phthalate disclosed in DE-A 43 08 087, to be added to said absorbents. Also suitable are esters of benzoic acid and phthalic acid with straight-chain alkanols of 1 to 8 carbon atoms, such as n-butyl benzoate, methyl benzoate, ethyl benzoate, dimethyl phthalate and diethyl phthalate, and heat transfer oils, such as biphenyl, diphenyl ether and mixtures of biphenyl and diphenyl ether or their chlorine derivatives and triarylalkenes, for example 4-methyl-4'-benzyldiphenylmethane and its isomers 2-methyl-2'-benzyldiphenylmethane, 2-methyl-4'-benzyldiphenylmethane and 4-methyl-2'-benzyldiphenylmethane and mixtures of such isomers. A suitable absorbent is a solvent mixture comprising biphenyl and diphenyl ether, preferably in the azeotropic composition, in particular comprising about 25% by weight of biphenyl and about 75% by weight of diphenyl ether, for example the commercially available diphyl. Frequently, this solvent mixture contains an added solvent such as dimethyl phthalate in an amount of from 0.1 to 25% by weight, based on the total solvent mixture. Other particularly suitable absorbents are octanes, nonanes, decanes, undecanes, dodecanes, tridecanes, tetradecanes, pentadecanes, hexadecanes, heptadecanes and octadecanes, tetradecanes having proven particularly suitable. It is advantageous if the absorbent used has the abovementioned boiling point on the one hand but at the same time does not have too high a molecular weight on the other hand. The molecular weight of the absorbent is advantageously 300 g/mol. The liquid paraffins of 8 to 6 carbon atoms which are described in DE-A 33 13 573 are also suitable. Examples of suitable commercial products are products sold by Haltermann, such as Halpasols i, such as Halpasol 250/340 i and Halpasol 250/275 i, and printing ink oils under the names PKWF and Printosol.

No particular restrictions are applicable when carrying out the absorption. All methods and conditions customary for a person skilled in the art may be used. Preferably, the gas mixture is brought into contact with the absorbent at from 1 to 50, preferably from 2 to 20, particularly preferably from 5 to 10, bar and from 0 to 100° C., in particular from 30 to 50° C. The absorption can be effected both in columns and in quench apparatuses. The cocurrent or countercurrent method may be employed. Suitable absorption columns are, for example, tray columns (having bubble trays and/or sieve trays), columns containing structured packings (for example sheet metal packings having a specific surface area of from 100 to 500 $m^2/m^3$, for example Mellapake® 250 Y) and packed columns (for example filled with Raschig packings). However, trickle and spray towers, graphite block absorbers, surface absorbers, such as thick-film and wetted-wall absorbers, and plate scrubbers, cross-film scrubbers and rotary scrubbers may also be used. It may also be advantageous to allow the absorption to take place in a bubble column with or without internals.

The separation of the propane and propene from the absorbent can be effected by stripping, flash evaporation (flashing) and/or distillation.

The separation of the propane and propene from the absorbent is preferably effected by stripping and/or desorption. The desorption can be carried out in a conventional manner by a pressure and/or temperature change, preferably at from 0.1 to 10, in particular from 1 to 5, particularly preferably from 1 to 3, bar and from 0 to 200° C., in particular from 20 to 100° C., particularly preferably from 30 to 50° C. A gas suitable for the stripping is, for example, steam, but oxygen/nitrogen mixtures are particularly preferred, for example air. With the use of air or oxygen/nitrogen mixtures in which the oxygen content is more than 10% by volume, it may be expedient to add, before or during the stripping process, a gas which reduces the explosion range. Gases having a specific heat capacity of >29 J/mol K at 20° C., for example methane, ethane, propane, propene, butane, pentane, hexane, benzene, methanol, ethanol and ammonia, carbon dioxide and water, are particularly suitable for this purpose. Bubble columns with and without internals are also particularly suitable for the stripping.

The separation of the propane and propene from the absorbent can also be effected by means of a distillation, it being possible to use the columns familiar to a person skilled in the art and containing stacked packings, dumped packings or corresponding internals. Preferred conditions during the distillation are a ressure from 0.01 to 5, in particular from 0.1 to 4, particularly preferably from 1 to 3, bar and a temperature (in the bottom) of from 50 to 300° C., in particular from 150 to 250° C.

Before it is used for feeding the reaction zone B, a product gas mixture A' obtained by stripping from the absorbent can be fed to a further process stage in order, for example, to reduce the losses of concomitantly stripped absorbent and thus simultaneously to protect the reaction zone B from absorbent. Such a removal of the absorbent can be effected by all process steps known to a person skilled in the art. An embodiment for such a removal which is preferred in the novel process is, for example, quenching of the exit stream from the stripping apparatus with water. In this case, the absorbent is washed out of this laden exit stream with water. This scrubbing or the quenching can be effected, for example, at the top of a desorption column over a liquid collecting tray by spraying water in the opposite direction or in a separate apparatus.

To support the separation effect, internals which enlarge the quench surface, as known to a person skilled in the art from rectifications, absorptions and desorptions, can be installed in the quench space.

Water is a preferred scrubbing agent in that it usually presents no problems in the downstream reaction zone B. After the water has washed the absorbent out of the exit stream laden with propane and propene, the water/absorbent mixture can be fed to a phase separation D and the treated exit stream can be fed as a product gas mixture A' to the reaction zone B.

Both the absorbent stripped $C_3$-free and the absorbent recovered in the phase separation can be reused for the absorption purpose.

The product gas mixture A or the product gas mixture A' produced therefrom can then be used in a manner known per se for feeding a heterogeneously catalyzed gas-phase oxidation of propene to acrolein and/or acrylic acid with a feed gas mixture A". Pure molecular oxygen, air or air enriched in oxygen may be added as an oxidizing agent.

In the novel process, the composition of the feed gas mixture A" is frequently adjusted with the concomitant use of the product gas mixture A' in such a way that it complies with the following molar ratios:

propane:propene:$N_2$:$O_2$:$H_2O$:others=0.5 to 20:1:0.1 to 40:0.1 to 10:0 to 20:0 to 1.

According to the invention, the abovementioned molar ratios are advantageously=2 to 10:1:0.5 to 20:0.5 to 5:0.01 to 10:0 to 1.

According to the invention, it is also advantageous if the abovementioned molar ratios are=3 to 6:1:1 to 10:1 to 3:0.1 to 2:0 to 0.5.

In principle, the heterogeneously catalyzed gas-phase partial oxidation of propylene to acrylic acid with molecular oxygen takes place in two steps in succession along the reaction coordinate, of which the first step leads to acrolein and the second one from acrolein to acrylic acid.

This reaction sequence in two steps in succession with respect to time opens up, in a manner known per se, the possibility of designing the reaction zone B in the novel process in two oxidation zones arranged in series, it being possible for the oxidic catalyst to be used to be optimized in each of the two oxidation zones. Thus, as a rule, a catalyst based on multimetal oxides containing the element combination Mo—Bi—Fe is preferred for the first oxidation zone (propylene→acrolein), while catalysts based on multimetal oxides containing the element combination Mo—V are usually preferred for the second oxidation zone (acrolein→acrylic acid).

Corresponding multimetal oxide catalysts for the two oxidation zones have been widely described in the past and are well known to a person skilled in the art. For example, EP-A 253 409 refers on page 5 to corresponding US patents.

Advantageous catalysts for the two oxidation zones are disclosed in DE-A 4 431 957 and DE-A 4431949. This applies in particular to those of the formula I in the abovementioned two publications. As a rule, the product mixture from the first oxidation zone is transferred to the second oxidation zone without intermediate treatment.

The two oxidation zones are therefore realized in the simplest manner by using a tube-bundle reactor within which catalyst load changes correspondingly along the individual catalyst tubes at the end of the first reaction step (such propylene partial oxidations suitable according to the invention as reaction zone B are described, for example, in EP-A 911313, EP-A 979813, EP-A 990636 and DE-A 2830765). If required, the catalyst load in the catalyst tubes can be interrupted by an inert bed.

However, the two oxidation zones are preferably realized in the form of two tube-bundle systems connected in series. These may be present in a reactor, the transition from one tube bundle to the other tube bundle being formed by a bed of inert material not housed in the catalyst tube (and expediently accessible). While a heating medium generally flows around the catalyst tubes, said heating medium does not reach an inert bed installed as described above. The two catalyst tube bundles are therefore advantageously housed in reactors spatially separated from one another. As a rule, an intermediate condenser is present between the two tube-bundle reactors in order to produce any acrolein postcombustion in the product gas mixture which leaves the first oxidation stage. Instead of tube-bundle reactors, plate-type heat exchanger reactors having brine cooling and/or evaporative cooling, as described, for example, in DE-A 19 929 487 and DE-A 19 952 964, can also be used.

The reaction temperature in the first oxidation zone is as a rule from 300 to 450° C., preferably from 320 to 390° C. The reaction temperature in the second oxidation zone is as a rule from 200 to 300° C., frequently from 220 to 290° C. The reaction pressure in both oxidation zones is expediently from 0.5 to 5, advantageously from 1 to 3, atm. The loading (1(S.T.P.)/1·h) of the oxidation catalysts with reaction gas is frequently from 1 500 to 2 500 $h^{-1}$ or up to 4 000 $h^{-1}$ in both oxidation zones. The propene loading may be from 100 to 200 1(S.T.P.)/1•h or more.

In principle, the two oxidation zones in the novel process can be designed as described, for example, in DE-A 19 837 517, DE-A 19 910 506, DE-A 19 910 508 and DE-A 19 837 519. Usually, the external heating in the two oxidation zones, optionally in multizone reactor systems, is adapted in a manner known per se to the specific composition of the reaction gas mixture and to the catalyst load.

The total amount of molecular oxygen necessary as an oxidizing agent for the reaction zone B required according to the invention can be added in its total amount to the feed gas mixture of the reaction zone B beforehand. However, it is of course also possible to add oxygen after the first oxidation zone.

A molar propylene:molecular oxygen ratio of from 1:1 to 1:3, frequently from 1:1.5 to 1:2, is preferably established in the first oxidation zone. Similar numerical values suitable for the molar acrolein:molecular oxygen ratio in the second oxidation zone (from 1:0.5 to 1:1.5 would be preferred).

In both oxidation zones, an excess of molecular oxygen generally has an advantageous effect on the kinetics of the gas-phase oxidation. In contrast to the conditions in the reaction zone A to be used according to the invention, the thermodynamic conditions are substantially not influenced by the molar ratio of reactants since the heterogeneously catalyzed gas-phase partial oxidation of propylene to acrylic acid takes place under kinetic control. For example, in the first oxidation zone, the propylene can in principle also be initially taken in a molar excess relative to the molecular oxygen. In this case, the excess propylene actually plays the role of a diluent gas.

In principle, however, the heterogeneously catalyzed gas-phase partial oxidation of propylene to acrylic acid can also be realized in a single oxidation zone. In this case, both reaction steps are carried out in an oxidation reactor which is loaded with a catalyst capable of catalyzing the reaction in both reaction steps. Of course, the catalyst load within the oxidation zone may also change continuously or abruptly along the reaction coordinate. In an embodiment of the reaction zone B to be used according to the invention and in the form of two oxidation zones connected in series, carbon dioxide and steam contained in the product gas mixture which leaves the first oxidation zone and formed as byproduct in the first oxidation zone can of course, if required, be separated partly or completely from said product gas mixture before it is passed further into the second oxidation zone. According to the invention, a procedure which does not require such a separation is preferably chosen.

Both pure molecular oxygen and molecular oxygen diluted with inert gas, such as $CO_2$, CO, noble gases, $N_2$ and/or saturated hydrocarbons, are suitable as the source of the molecular oxygen which is required in the reaction zone B and mixed with the product gas mixture A or A' before it is used for feeding the reaction zone B.

Expediently, air is used as an oxygen source at least for covering a part of the molecular oxygen demands.

In the novel process, the product gas mixture A' advantageously comprises substantially only propane and propylene (the amount of components differing therefrom is expediently $\leq 5\%$ by volume or $\leq 2\%$ by volume) and the source of molecular oxygen used for the downstream reaction zone B comprises exclusively air, which as a rule is compressed (typically 2-3 bar) and heated (typically 130° C.-180° C.) before being added.

By metering cold air into the hot product gas mixture A', cooling of the product gas mixture A' can also be effected in a direct manner in the novel process.

If acrolein is the desired product, the second oxidation zone is expediently no longer used in the reaction zone B.

The product gas mixture B leaving the reaction zone B to be used according to the invention is as a rule composed substantially of the desired product acrolein or acrylic acid or a mixture thereof with acrolein, unconverted molecular oxygen, propane, unconverted propene, molecular nitrogen, steam formed as a byproduct and/or present as diluent gas, carbon oxides formed as byproduct and/or present as diluent gas, and small amounts of lower aldehydes, lower alkanecarboxylic acids (e.g. acetic acid, formic acid and propionic acid) and maleic anhydride, benzaldehyde, hydrocarbons and other inert diluent gases.

The desired product can be isolated from the product gas mixture B in a manner known per se (for example by partial condensation of the acrylic acid or by absorption of acrylic acid in water or in a high-boiling hydrophobic organic solvent or by absorption of acrolein in water or in aqueous solutions of lower carboxylic acids and subsequent working-up of the absorbates; alternatively, the product gas mixture B can also be subjected to fractional condensation; cf. for example EP-A 117146, DE-A 4308087, DE-A 4335172, DE-A 4436243, DE-A 19 924 532 and DE-A 19 924 533).

Unconverted propylene and/or acrolein are, if required, also separated off and are recycled to the reaction zone B.

Otherwise, those major components remaining after isolation of the desired product which differ from acrylic acid and acrolein can, depending on requirements and on dehydrogenation catalyst used, each be separated off by themselves and/or recycled with the propane as recycle gas (recycle stream) into the reaction zone A in order to influence the conversion in the dehydrogenation reaction there, as described. However, the unconverted propane can of course also be recycled as a mixture with the unconverted propylene (as recycle stream) into the reaction zone A. When the novel process is carried out continuously, a continuous conversion of propane in acrylic acid (acrolein) thus takes place.

The separation of propane and propene from the residual gas remaining after isolation of the desired product (said residual gas contains, as a rule, $O_2$, CO, $CO_2$, $H_2O$, $N_2$, noble gases and other lower aldehydes, lower alkanecarboxylic acids (e.g. acetic acid, formic acid and propionic acid) and maleic anhydride, benzaldehyde and hydrocarbons) can be effected, as described above, by absorption with subsequent desorption and/or stripping (and reuse of the absorbent) in a high-boiling hydrophobic organic solvent. Further possibilities for separation are adsorption, rectification and partial condensation.

With the use of dehydrogenation catalysts which are sensitive to oxygen or oxygen-containing compounds, these oxygenates are separated from the recycle gas before the recycle gas is recycled into the stage A. Such a separation of oxygen may also be expedient for avoiding oxidation of the propane in the dehydrogenation stage A. The dehydrogenation catalysts of DE-A 19 937 107 are not sensitive to oxygenates (in particular those according to examples 1 to 4 of the DE-A).

Another possibility for separation is fractional distillation, as likewise mentioned above. A fractional distillation under superatmospheric pressure at low temperatures is preferably carried out. The pressure to be used is, for example, from 10 to 100 bar. The rectification columns used may be columns containing dumped packings, tray columns or columns containing stacked packings. Suitable tray columns are those having dual-flow trays, bubble trays or valve trays. The reflux ratio may be, for example, from 1 to 10. Other possibilities for separation are, for example, extraction under pressure, pressure swing adsorption, scrubbing under pressure and partial condensation.

According to the invention, it is of course also possible to recycle the total amount of residual gas (as a recycle stream) into the reaction zone A, for example when a removal of secondary components is integrated downstream of the reaction zone A. In this case, the outlet for gas components other than propane, propene and molecular oxygen may be present exclusively between the product gas mixture A and the product gas mixture A'.

Of course, a further outlet can be set up downstream of the isolation of desired product. If the recycle gas recycled into the propane dehydrogenation contains carbon monoxide, this can be combusted catalytically to give $CO_2$ before being supplemented with fresh propane. The heat of reaction liberated can be used for heating to the dehydrogenation temperature.

A catalytic postcombustion of CO contained in the residual gas to give $CO_2$ may also be advisable when separation of oxides of carbon from the residual gas before it is recycled as recycle gas into the propane dehydrogenation is desired, since $CO_2$ is comparatively simple to separate off (for example by scrubbing with the basic liquid).

It is also possible to adopt a procedure in which a part of the residual gas is recycled unchanged into the propane dehydrogenation and propane and propene as a mixture is separated off only from the remaining part and likewise recycled into the propane dehydrogenation and/or into the reaction zone B. In the latter case, the remaining part of the residual gas is expediently combined with the product gas mixture A or A'.

In a fractional distillation of the residual gas, the operating line can be positioned, for example, so that substantially all those components whose boiling point is lower than the boiling point of propene can be separated off and taken off at the top of the column in that part of the rectification column which has an ascending stream. These components would primarily be the oxides of carbon CO and $CO_2$ and unconverted oxygen and ethylene, and methane and $N_2$.

It should be once again stated that it is essential to the invention that the propane-containing residual gas recycled into the reaction zone A during normal operation is recycled at least partly (preferably completely in the case of a single reactor A) by a route other than via the reaction zone A into the reaction zone B during a nonoperating phase in the reaction zone A and at the same time the loss of propene is at least partly or preferably completely supplemented from another source.

Both this supplementation and the recycling are preferably carried out in this case so that, where a separation apparatus is integrated downstream of the reaction zone A during normal operation, this supplementation and this recycling also have to pass through this separation apparatus during this nonoperating phase. Of course, both this supplementation and this recycling can also be carried out behind the separation apparatus.

In the case of the preparation of acrylic acid from propane, the novel process is frequently carried out in such a way that, in the product gas mixture B, at least 70, preferably at least 85, mol % of the total amount of molecular oxygen fed in in the various reaction zones has been reacted.

Preferably, the molar ratio acrolein:molecular oxygen: steam propane:molecular nitrogen:other diluent gases is 1:0.5 to 1.5:0.1 to 2:0.5 to 6:1 to 10:0 to 5 in the second oxidation zone of the reaction zone B.

It is advantageous if multimetal oxide catalysts which correspond to those of the formula I or II or III from DE-A 19 910 506 are used in the first oxidation zone of the reaction zone B and if multimetal oxide catalysts which correspond to those of the formula I or I' or II from DE-A 19 910 508 are used in the second oxidation zone of the reaction zone B.

Catalyst geometries suitable according to the invention for the first and second oxidation zones are those which are recommended in DE-A 19 910 506 and in DE-A 19 910 508, respectively.

Furthermore, the tube-bundle reactors recommended for the reaction zone B may be operated both cocurrently and countercurrently with regard to the flow of reaction gas and heating medium (e.g. salt bath). Cross-flows can of course also be superposed. It is particularly advantageous if the heating medium is fed in a meander-like manner around the catalyst tube, which feed, considered over the reactor, may in turn be cocurrent or countercurrent to the reaction gas mixture.

As a rule, reactors having passivated inner surfaces are used for the reaction zone A. The passivation can be effected, for example, by applying sintered alumina to the inner surface prior to the dehydrogenation. It can however also be effected in situ by adding small amounts of passivating assistants (e.g. sulfides) to the reaction gas mixture.

The novel process is preferred when a product mixture A' which comprises substantially only at least one paraffinic hydrocarbon A and at least one paraffinic hydrocarbon A' is used. Of course, a purge stream may also be used for separating off secondary components in the novel process.

EXAMPLES

FIG. 1 attached to this document schematically shows a novel procedure in normal operation. The reaction zone A should comprise only one reactor A.

Figure 2:
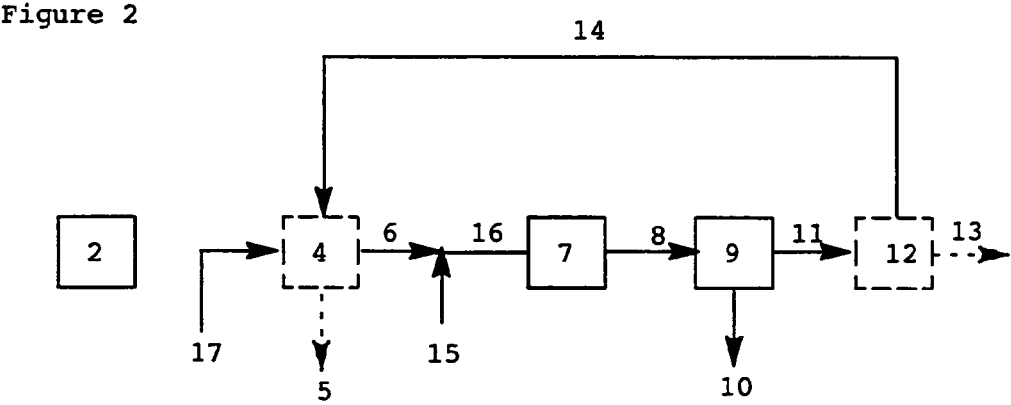

FIG. 2 attached to this document shows a novel nonoperating phase associated with FIG. 1. There, the numerals represent the following:

1=fresh paraffinic hydrocarbon A and, if required, other starting materials used for the dehydrogenation and/or oxydehydrogenation;

2=reaction zone A (for oxydehydrogenation and/or dehydrogenation);

3=product gas mixture A, containing paraffinic hydrocarbon A and olefinic hydrocarbon A';

4=any concomitantly used separation zone for separating off secondary components other than paraffinic hydrocarbon A and olefinic hydrocarbon A';

5=any secondary components separated off in the separation zone 4;

6=either the product mixture A or production mixture A', depending on the use of 4;

16=feed mixture of reaction zone B;

15=starting materials (e.g. molecular oxygen) required in addition to the product mixture A or product mixture A' for the preparation of 16;

7=reaction zone B;

8=product mixture B;
9=isolation of desired product from product mixture B;
10=desired product;
11=residual mixture containing paraffinic hydrocarbon A;
12=any separation apparatus used for secondary components other than paraffinic hydrocarbon A;
13=any byproducts separated off;
14=recycle stream containing paraffinic hydrocarbon A;
17=olefinic hydrocarbon A' originating from a source other than reaction zone A.

Figure 3:
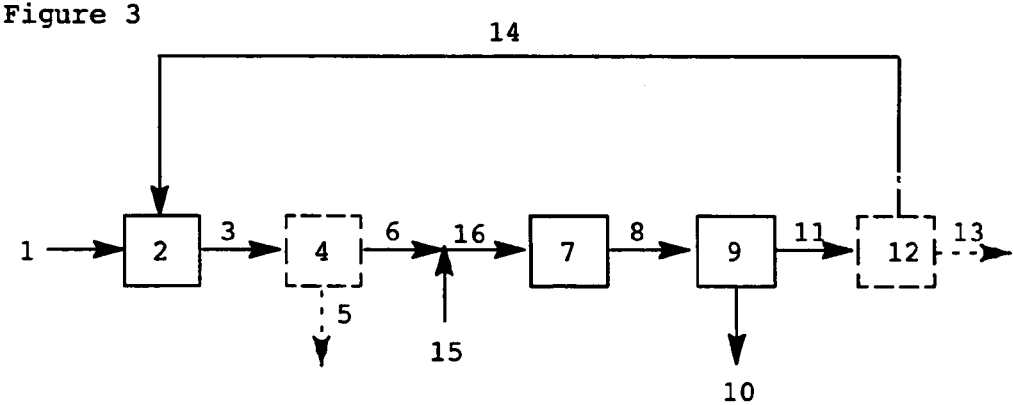

FIG. 3 attached to this document schematically shows a novel procedure in normal operation. The reaction zone A should comprise more than one reactor A.

Figure 4:
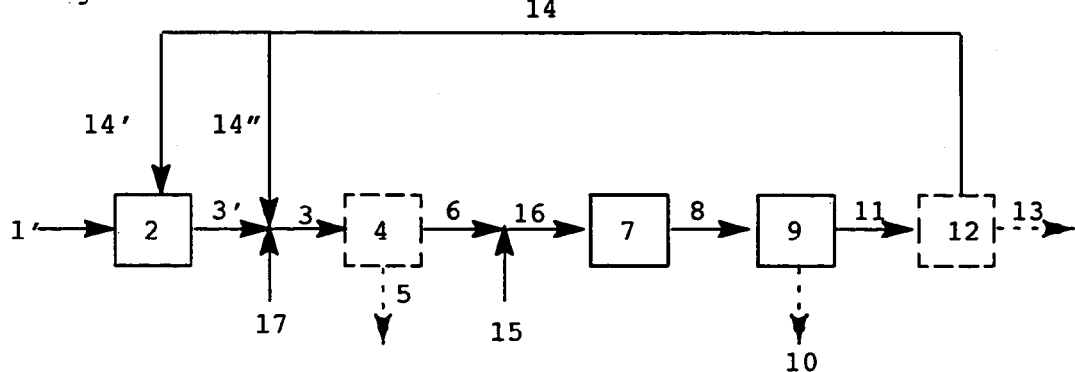

FIG. 4 attached to this document shows a novel nonoperating phase associated with FIG. 3. Identical numerals have the same meaning as in FIGS. 1 and 2. Otherwise, the following numerals represent:

1'=a smaller amount of fresh paraffinic hydrocarbon A corresponding to the nonoperating part in the reaction zone A and of any other starting materials used for the dehydrogenation and/or oxydehydrogenation;
3'=reduced amount of product gas mixture A, containing paraffinic hydrocarbon A and olefinic hydrocarbon A';
17=olefinic hydrocarbon A' originating from a source other than reaction zone A and compensating the reduced production in 2;
14'=amount of recycle stream containing paraffinic hydrocarbon A, which amount is reduced according to the nonoperating part in 2;
14"=the part of the recycle stream containing the paraffinic hydrocarbon A and corresponding to the nonoperating part in 2 (14'+14"=14).

The invention claimed is:

1. A process for the preparation of one or more partial oxidation products, one or more partial ammoxidation products, or both, of at least one olefinic hydrocarbon A', comprising
   A) subjecting, in a first reaction zone A, at least one paraffinic hydrocarbon A to a partial dehydrogenation, oxydehydrogenation, or both, to form a product mixture A which comprises at least one paraffinic hydrocarbon A and at least one olefinic hydrocarbon A' formed by the partial dehydrogenation, oxydehydrogenation, or both,
   B) optionally separating from the product mixture A at least a portion of the components other than the paraffinic hydrocarbon A and the olefinic hydrocarbon A' to form a product mixture A', and feeding either the product mixture A, when said separating is not carried out, or the product mixture A', when said separating is carried out, to an oxidation, ammoxidation, or both, zone B and, subjecting the olefinic hydrocarbon A' to partial oxidation, ammoxidation, or both, to form a product mixture B which comprises at least one partial oxidation, ammoxidation, or both, product B of the at least one olefinic hydrocarbon A',
   C) separating partial oxidation, ammoxidation, or both, product B from the product mixture B in a working-up zone C and recycling at least a portion of the at least one paraffinic hydrocarbon A in the product mixture B into the reaction zone A and
   D) intermittently not operating at least a part of the reaction zone A wherein, while at least a part of the reaction zone A is not operating, the oxidation, ammoxidation, or both, in zone B is further carried out and a production loss of the at least one olefinic hydrocarbon A' while at least a part of reaction zone A is not operated is at least partly compensated by feeding at least one olefinic hydrocarbon A' originating from a source other than the reaction zone A, and optionally one or more paraffinic hydrocarbons A originating from a source other than the reaction zone A, to the oxidation, ammoxidation, or both, zone B and then recycling at least a portion of the at least one paraffinic hydrocarbon A present in the product mixture B of the oxidation, ammoxidation, or both, zone B, as paraffinic recycle hydrocarbon A, not via the reaction zone A, into the oxidation, ammoxidation, or both, zone B.

2. The process as claimed in claim 1, wherein the reaction zone A comprises only one reactor A for the partial dehydrogenation, oxydehydrogenation, or both.

3. The process as claimed in claim 2, wherein the at least one paraffinic hydrocarbon A is subjected to a heterogeneously catalyzed partial dehydrogenation in the one reactor A.

4. The process as claimed in claim 1, wherein the at least one paraffinic hydrocarbon A is propane and the at least one olefinic hydrocarbon A' is propylene.

5. The process as claimed in claim 1, wherein said optional separating is carried out, and said at least a portion of the components other than the paraffinic hydrocarbon A and the olefinic hydrocarbon A' therein are separated from said product mixture A in a separation zone to form a product mixture A'.

6. The process as claimed in claim 5, wherein said at least a portion is substantially the total amount of said components that are separated from said product mixture A in a separation zone to form a product mixture A'.

7. The process as claimed in claim 5, wherein the olefinic hydrocarbon A' originating from a source other than the reaction zone A is fed to the oxidation, ammoxidation, or both, zone B by passing through the separation zone.

8. The process as claimed in claim 7, wherein the at least one portion of the at least one paraffinic hydrocarbon A present in the product mixture B of the oxidation, ammoxidation, or both, zone B is recycled to the oxidation, ammoxidation, or both, zone B, with exclusion of the reaction zone A, by passing through the separation zone.

9. The process as claimed in claim 1, wherein the olefinic hydrocarbon A' originating from a source other than the reaction zone A is chemical grade propylene, polymer grade propylene or both.

10. The process as claimed in claim 1, further comprising forming acrolein, acrylic acid, or both.

11. The process as claimed in claim 1, wherein said at least one paraffinic hydrocarbon A is one or more saturated hydrocarbons having not more than 10 carbon atoms, said at least one olefinic hydrocarbon A' is one or more hydrocarbons having at least one ethylenically unsaturated double bond and containing not more than 10 carbon atoms, and said product B is at least one partial oxidation and/or ammoxidation product selected from the group consisting of acrolein, acrylic acid, ethylene oxide, methacrolein, methacrylic acid, propylene oxide, acrylonitrile and methacrylonitrile.

12. The process as claimed in claim 11, wherein said at least one paraffinic hydrocarbon A is at least one of ethane, propane, and a butane, and said at least one olefinic hydrocarbon A' is at least one of ethylene, propylene and a butene.

* * * * *